United States Patent
Jaffe

(10) Patent No.: US 10,448,863 B2
(45) Date of Patent: Oct. 22, 2019

(54) SYSTEM AND METHOD FOR MONITORING COMPOSITION IN A SIDESTREAM SYSTEM USING A PUMP AND DETECTOR WITH CONTROL ELECTRONICS THAT ARE TIGHTLY INTEGRATED

(71) Applicant: KONINKLIJKE PHILIPS N.V., Eindhoven (NL)

(72) Inventor: Michael Brian Jaffe, Cheshire, CT (US)

(73) Assignee: Koninklijke Philips N.V., Eindhoven (NL)

( * ) Notice: Subject to any disclaimer, the term of this patent is extended or adjusted under 35 U.S.C. 154(b) by 163 days.

(21) Appl. No.: 14/361,551

(22) PCT Filed: Nov. 27, 2012

(86) PCT No.: PCT/IB2012/056753
§ 371 (c)(1),
(2) Date: May 29, 2014

(87) PCT Pub. No.: WO2013/080121
PCT Pub. Date: Jun. 6, 2013

(65) Prior Publication Data
US 2014/0316241 A1    Oct. 23, 2014

Related U.S. Application Data

(60) Provisional application No. 61/565,549, filed on Dec. 1, 2011.

(51) Int. Cl.
A61B 5/08 (2006.01)
A61M 16/06 (2006.01)
(Continued)

(52) U.S. Cl.
CPC ............ *A61B 5/082* (2013.01); *A61B 5/0059* (2013.01); *A61M 16/024* (2017.08); *A61M 16/0672* (2014.02); *A61M 16/0666* (2013.01); *A61M 16/1075* (2013.01); *A61M 16/16* (2013.01); *A61M 2016/103* (2013.01); *A61M 2016/1025* (2013.01); *A61M 2016/1035* (2013.01); *A61M 2205/3306* (2013.01); *A61M 2205/502* (2013.01)

(58) Field of Classification Search
CPC ..................................................... A61B 5/082
See application file for complete search history.

(56) References Cited

U.S. PATENT DOCUMENTS 6,041,777 A * 3/2000 Faithfull ........... A61M 16/0054
128/200.24
6,325,978 B1 12/2001 Labuda et al.
(Continued)

FOREIGN PATENT DOCUMENTS

CN    2070446 U    1/1991
CN    101393199 A    3/2009
(Continued)

*Primary Examiner* — Rochelle D Turchen

(57) ABSTRACT

A system and method are configured to monitor composition of a flow of breathable gas being provided to a subject. The monitoring is accomplished in a sidestream configuration in which control of a pump and a detector are implemented in a tightly integrated controller.

20 Claims, 9 Drawing Sheets

(51) Int. Cl.
    *A61B 5/00*     (2006.01)
    *A61M 16/00*     (2006.01)
    *A61M 16/10*     (2006.01)
    *A61M 16/16*     (2006.01)

(56) References Cited

U.S. PATENT DOCUMENTS

| | | | |
|---|---|---|---|
| 6,632,402 | B2 | 10/2003 | Blazewicz et al. |
| 6,954,702 | B2 * | 10/2005 | Pierry ............... A61B 5/083 422/94 |
| 7,748,280 | B2 | 7/2010 | Jaffe et al. |
| 2010/0168599 | A1 | 7/2010 | Esposito et al. |
| 2010/0286546 | A1 * | 11/2010 | Tobola ............... A61B 5/6805 600/534 |
| 2011/0253136 | A1 * | 10/2011 | Sweeney ............ A61M 16/024 128/203.12 |

FOREIGN PATENT DOCUMENTS

| | | |
|---|---|---|
| WO | 2008005907 A2 | 1/2008 |
| WO | 2009134181 A1 | 11/2009 |
| WO | 2010128914 A1 | 11/2010 |
| WO | 2011055250 A2 | 5/2011 |

\* cited by examiner

SYSTEM AND METHOD FOR MONITORING COMPOSITION IN A SIDESTREAM SYSTEM USING A PUMP AND DETECTOR WITH CONTROL ELECTRONICS THAT ARE TIGHTLY INTEGRATED

CROSS-REFERENCE TO PRIOR APPLICATIONS

This application is the U.S. National Phase application under 35 U.S.C. § 371 of International Application No. PCT/IB2012/056753, filed on Nov. 27, 2012, which claims the benefit of U.S. Provisional Patent Application No. 61/565,549, filed on Dec. 1, 2011. These applications are hereby incorporated by reference herein.

BACKGROUND

1. Field

The present disclosure pertains to a method and apparatus for monitoring the composition of a measurement flow of breathable gas received in a sidestream manner with a pump and detector assembly that are controlled by control electronics that are tightly integrated.

2. Description of the Related Art

Systems that monitor composition of gas by obtaining a measurement flow of breathable gas from a therapeutic flow of breathable gas in a sidestream manner are known. Generally, these systems require a pump to draw the measurement flow of breathable gas through a sampling chamber where measurements are taken, and a detector assembly to measure composition of the gas. In conventional systems, the pump and the detector assembly are separate and discrete systems each with their own control system. As a result, control over these components is accomplished via two separate and discrete sets of control electronics.

SUMMARY

Accordingly, one or more aspects of the present disclosure relate to a detector device configured to measure composition of a flow of breathable gas received from a respiratory circuit. In some embodiments, the detector device comprises a housing, a flow path, a radiation source, a sensor assembly, a pump, and one or more processors. The flow path is for the flow of breathable gas, and has an inlet and an outlet. The radiation source is housed within the housing and is configured to emit electromagnetic radiation into the flow path. The sensor assembly is housed within the housing and is configured to receive electromagnetic radiation that has been emitted by the radiation source and has passed through the flow path. The sensor assembly is further configured to generate output signals conveying information related to one or more parameters of the received electromagnetic radiation. The pump comprises a pump motor and a pump actuator. The pump motor is carried by the housing. The pump actuator is carried by the housing, and is configured to be driven by the pump motor to draw the flow of breathable gas through the flow path. The one or more processors are housed within an individual housing compartment formed within the housing, and are configured to execute modules. The module comprises a source module, a sensor module, a pump actuation module, and a pump reading module. The source module is configured to drive the radiation source. The sensor module is configured to read the output signals generated by the sensor assembly. The pump actuation module is configured to drive the pump motor. The pump reading module is configured to obtain information related to one or more operating parameters of the pump.

Yet another aspect of the present disclosure relates to a method of measuring composition of a flow of breathable gas received from a respiratory circuit. In some embodiments, the method comprises emitting electromagnetic radiation from a radiation source into a flow path for the flow of breathable gas; receiving the emitted electromagnetic radiation after it has passed through the flow path; generating output signals from a sensor assembly that convey information related to one or more parameters of the received electromagnetic radiation; drawing the flow of breathable gas through the flow path with a pump that includes a pump motor and a pump actuator, wherein the radiation source, the sensor assembly, and the pump are housed in and/or carried by a single housing; and executing modules on one or more processors that are contained within a single compartment of the housing. The modules comprise a source module, a sensor module, a pump actuation module, and a pump reading module. The source module is configured to drive the radiation source. The sensor module is configured to read the output signals generated by the sensor assembly. The pump actuation module is configured to drive the pump motor. The pump reading module is configured to obtain information related to one or more operating parameters of the pump.

Still another aspect of present disclosure relates to a detector device for measuring composition of a flow of breathable gas received from a respiratory circuit. In some embodiments, the detector device comprises means for emitting electromagnetic radiation into a flow path for the flow of breathable gas; means for receiving the emitted electromagnetic radiation after it has passed through the flow path; means for generating output signals that convey information related to one or more parameters of the received electromagnetic radiation; means for drawing the flow of breathable gas through the flow path, the means for drawing comprising a pump motor and a pump actuator, wherein the means for emitting, the means for generating, the pump motor, and the pump actuator are housed in and/or carried by a single housing; and means for executing modules, the means for executing being contained within a single compartment of the housing. The modules comprise a source module, a sensor module, a pump actuation module, and a pump reading module. The source module is configured to drive the radiation source. The sensor module is configured to read the output signals generated by the sensor assembly. The pump actuation module is configured to drive the pump motor. The pump reading module is configured to obtain information related to one or more operating parameters of the pump.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
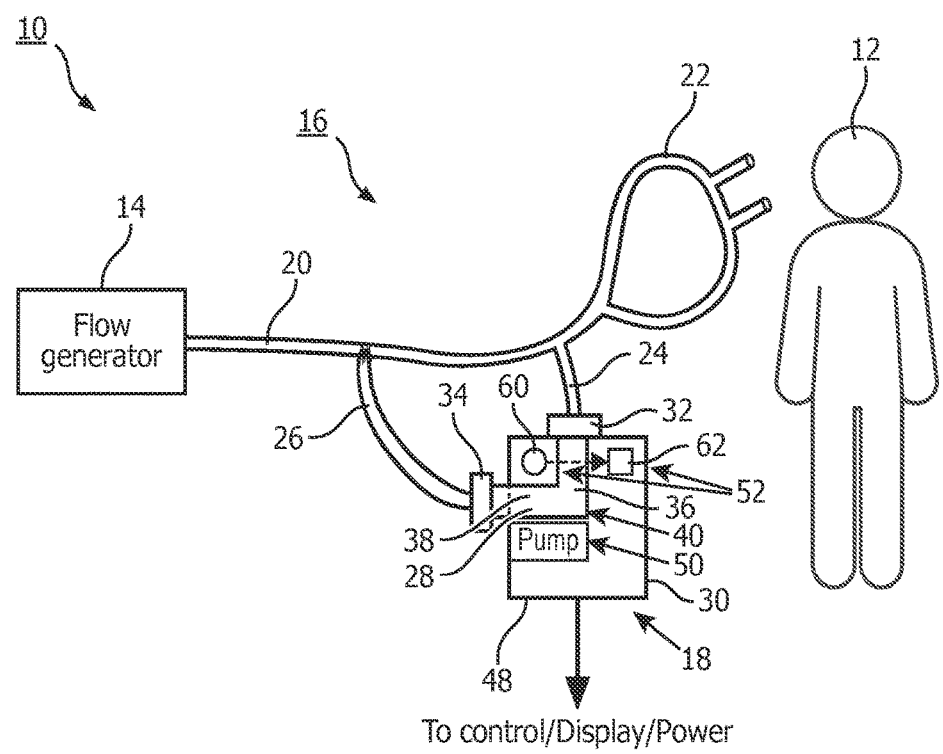
FIG. 1 is a system configured to monitor a composition of a flow of breathable gas.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to monitor composition of a flow of breathable gas being provided to a subject 12. System 10 may be configured such that a measurement flow of breathable gas is diverted in order to monitor composition of the flow of breathable gas, and then the measurement flow of breathable gas is returned to the flow of breathable gas. This will tend to conserve the constituent gases within the flow of breathable gas, which may be significant in instances where the flow of breathable gas is being used to deliver medicaments or drugs (e.g., relatively expensive anesthetic, and/or other medicaments or drugs). Since the measurement flow of breathable gas will tend to have contaminants (e.g., mucus blood, medications, condensate or other materials), routing the measurement flow of breathable gas back into the flow of breathable gas constitutes a placement solution for the contaminants. This, however, is not intended to be limiting, as the measurement flow of breathable gas may not be returned to the flow of breathable gas in some embodiments. Instead, the measurement flow of breathable gas may be exhausted (e.g., through a filter or other exhaust). In some embodiments, system 10 may include one or more of a flow generator 14, a respiratory circuit 16, a measurement circuit 18, and/or other components.

Flow generator 14 is configured to generate the flow of breathable gas for delivery to the airway of subject 12. Flow generator 14 is configured to control one or more parameters of the flow of breathable gas. The parameter(s) controlled may include one or more of pressure, temperature, flow rate, humidity, velocity, acoustics, and/or other parameters. In some embodiments, flow generator 14 is configured to control the composition of the flow of breathable gas by blending gases from a two or more gas sources (e.g., to control oxygen content), by adding a drug or medicament (e.g., in nebulized and/or aerosolized form), and/or by other techniques. To pressurize the flow of breathable gas, flow generator 14 may include one or more of a blower, a bellows, a pressurized canister or Dewar, a wall gas source, and/or other sources of pressure.

Respiratory circuit 16 is configured to deliver the flow of breathable gas from flow generator 14 to the airway of subject 12. Respiratory circuit 16 may include one or more of a conduit 20, a subject interface 22, and/or other components. Conduit 20 is configured to convey the flow of breathable gas from flow generator 14 to subject interface 22. Conduit 20 interfaces with flow generator 14 to receive the flow of breathable gas therefrom, and provides a flow path from flow generator 14 to subject interface 22. Conduit 20 may be resiliently flexible. Subject interface 22 may engage one or more orifices of the airway of subject 12 in a sealed or unsealed manner. Some examples of subject interface 22 may include, for example, an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present invention is not limited to these examples, and contemplates implementation of any subject interface. For example, sidestream gas sampling (e.g., as shown and described with respect to system 10) may be used in conjunction with an airway adapter which is in-line with both expiratory and inspiratory gases, a facemask from which a tap is often made and a nasal cannula as shown in FIG. 1 which may be used to sample a respiratory gas (e.g. CO2) and/or to deliver a therapeutic gas (e.g., oxygen).

Measurement circuit 18 is configured to draw a measurement flow of breathable gas off from the flow of breathable gas in respiratory circuit 16 to monitor the compositions of the flow of breathable gas. The measurement flow of breathable gas may be between about 30 ml/min and about 250 ml/min. In some embodiments, the measurement flow of breathable gas is about 50 ml/min. Measurement circuit 18 may return some or all of the gas in the measurement flow of breathable gas back to the flow of breathable gas within respiratory circuit 16. Measurement circuit 18 may include one or more of a circuit inlet 24, a circuit outlet 26, a flow path element 28, a detector device 30, and/or other components.

Circuit inlet 24 is configured to receive a portion of the gas in the flow of breathable gas within respiratory circuit 16 as a measurement flow of breathable gas, and to guide the measurement flow of breathable gas to flow path element 28. Circuit outlet 26 is configured to receive the measurement flow of breathable gas after it has passed through flow path element 28. Circuit outlet 26 may be configured to provide the measurement flow of breathable gas back into respiratory circuit 16. Circuit inlet 24 and circuit outlet 26 may be conduits similar in structure (or the same as) conduit 20. Circuit outlet 26 may be a connector or not even exist if the flow is to pass into the atmosphere. The interface(s) between one or both of circuit inlet 24 and conduit 20, and circuit outlet 26 and conduit 20 may be releasable.

Figure 2:
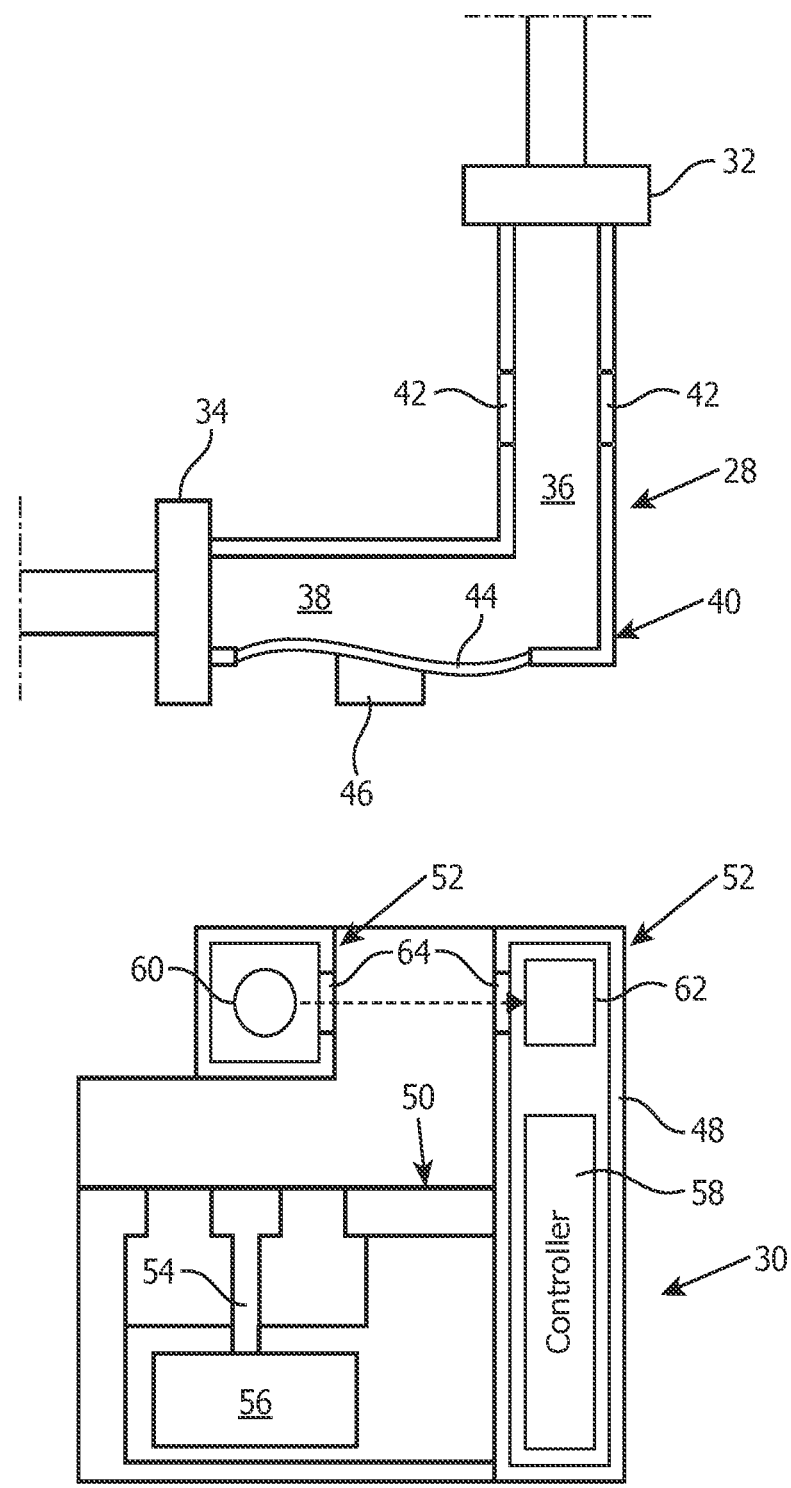
FIG. 2 is a detector assembly and flow path element configured to monitor a composition of a flow of breathable gas.

FIG. 2 provides a more detailed schematic of flow path element 28 and detector device 30. In the view shown in FIG. 2, flow path element 28 has been disengaged from detector device 30 (FIG. 1 depicts flow path element 28 releasably engaged with detector device 30). As can be seen in FIG. 2, flow path element 28 includes an inlet 32, an outlet 34, and provides an enclosed flow path between inlet 32 and outlet 34. Inlet 32 is configured to interface with circuit inlet 24, and outlet 34 is configured to interface with circuit outlet 26 such that the enclosed flow path formed by flow path element 28 carries the measurement flow of breathable gas through flow path element 28 from inlet 32 to outlet 34. The walls of flow path element 28 between inlet 32 and outlet 34 may be formed of substantially rigid plastic and/or polymer materials. Flow path element 28 further comprises one or more of a sampling chamber 36, a pump section 38, a device interface 40, and/or other components.

Although detector device 30 and flow path element 28 are shown exploded from each other in FIG. 2, this is not intended to be limiting. In some embodiments, detector device 30 and flow path element 28 are not removably coupled, but instead are formed either integrally or with a permanent (or substantially permanent) attachment therebetween. In some embodiments in which detector device 30 and flow path element 28 are not removably coupled, these components (and/or their parts) may be cleaned or sterilized via suitable cleaning and sterilization methods.

Sampling chamber 36 is configured to facilitate measurements of the composition of the measurement flow of breathable gas to be taken. As such, sampling chamber 36 includes windows 42. Windows 42 are optically transparent to electromagnetic radiation at one or more wavelengths used to measure the composition of gas within sampling chamber 36. By way of non-limiting example, windows 42 may be formed from sapphire, IR transmissive plastics, and/or other materials.

Pump section 38 is configured to generate flow through flow path element 28 from inlet 32 to outlet 34. In some embodiments, pump section 38 operates as the head of a membrane pump system to generate flow through flow path element 28. Pump section 38 may include one or more of a membrane 44, an actuator interface 46, and/or other components. Membrane 44 is configured to be movable to generate flow through pump section 38. Actuator interface 46 is configured to releasably engage a pump actuator 54 associated with detector device 30 to actuate membrane 44 in a manner that causes movement by membrane 44 resulting in flow through flow path element 28.

For embodiments in which flow path element 28 is detachable/replaceable, the enclosed flow path formed by flow path element 28 enables flow path element 28 to be used for a subject individually. This means that for another subject, and/or for another usage session, flow path element 28 can be swapped for another (e.g., new) flow path element. It will be appreciated that in such embodiments, the components of flow path element 28 may be relatively inexpensive from a materials and/or manufacturing perspective. For example, flow path element 28 may not include any sensor or radiation emitter elements, and may not include any parts of a motor that operates to drive the pump formed by pump section 38. In some embodiments, flow path element 28 does not include any processing and/or storage components, to maintain a relatively low cost. As such, flow path element 28 may be replaced without impacting operation of the active components of detector device 30 (e.g., a composition sensor and a pump motor, as described herein). This may enhance the usability of detector device 30 in a setting in which detector device 30 is implemented in respiratory circuits for a plurality of subjects. However, flow path element 28 may include a memory element (e.g., read only or read/write) for storage of calibration information relating to the windows (e.g., absorption characteristics for use in infrared measurements; calibration factors for signal correction for use in luminescence quenching measurements; and/or other calibration information) or other components of flow path element. Such a memory element could store usage information to help alert detector device 30, a system including detector device 30, and/or a user of reuse of a component intended to be single-use and/or for use by a single subject, such as flow path element 28.

As can be seen in FIG. 2, detector device 30 is configured to cause the measurement flow of breathable gas to be drawn through flow path element 28, monitor the composition of the gas within sampling chamber 36, and/or to perform other functions. Detector device 30 may include one or more of a housing 48, element dock 50, a detector assembly 52, a pump actuator 54, pump motor 56, a controller 58, and/or other components.

Housing 48 is configured to house some or all of the components of detector device 30. Housing 48 is formed of a rigid material, such as a metallic, plastic or polymer. Housing 48 may provide mechanical protection, fluid protection, and/or other types of protection for the components of detector device 30.

In embodiments in which flow path element 28 is removably engaged with detector device 30, element dock 50 is configured to removably engage flow path element 28. Element dock 50 may be formed by housing 48. For example, housing 48 may have a shape at element dock 50 that accommodates the external shape of flow path element 28. Element dock 50 secures flow path element 28 to detector device 30, and places the various components of flow path element 28 and detector device 30 in the proper relative positions for use. In securing flow path element 28 to detector device 30, element dock 50 may engage flow path element 28 with one or more of a threaded engagement, an interlocking engagement, a friction fit, a snap fit, a latch, and/or other mechanisms for releasable engagement.

Detector assembly 52 is configured to monitor the composition of gas in sampling chamber 36. For example, detector assembly 52 may be configured to detect a relative level of carbon dioxide, a relative level of oxygen, anesthetic agents (e.g., nitrous oxide, halothane, desflurane, etc.), trace gases (e.g., PPM or PPB concentrations), and/or relative levels of other gas constituents within sampling chamber 36. Detector assembly may include one or more of a radiation source 60, a sensor assembly 62, windows 64, and/or other components.

Radiation source 60 is configured to emit electromagnetic radiation through sampling chamber 36 (e.g., through windows 64). The electromagnetic radiation emitted travels through the gas within sampling chamber 36, and out of sampling chamber 36 on the other side of sampling chamber 36. The electromagnetic radiation generated by radiation source 60 may have a specified set of one or more wavelengths used to detect one or more gases. By way of non-limiting example, infrared electromagnetic radiation from radiation source 60 may be implemented to monitor the relative level of carbon dioxide within sampling chamber 36. Although not shown in FIG. 2, radiation source 60 may include one or more optical elements configured to guide the emitted electromagnetic radiation into sampling chamber 36. Such elements may include one or more of a mirror, a lens, and/or other optical elements.

Sensor assembly 62 is configured to receive electromagnetic radiation emitted by radiation source 60 that has passed through sampling chamber 36, and the gas contained therein, and to generate output signals conveying information related to one or more parameters of the received electromagnetic radiation. The one or more parameters may include one or more of intensity, flux, luminescence, phase, and/or other parameters. Sensor assembly 62 includes one or more photosensitive sensors configured to generate output signals related to the intensity of received electromagnetic radiation. Sensor assembly 62 may include one or more optical elements to filter, shape, and/or guide the electromagnetic radiation to the one or more photosensitive sensors. Such optical elements may include one or more of a mirror, a half-mirror, a wavelength filter, a polarizer, a lens, and/or other optical elements. For example, the output signals may convey information related to intensity of the electromagnetic radiation in a wavelength range that is absorbed by a gaseous constituent of interest (e.g., carbon dioxide), and the intensity of electromagnetic radiation in a reference wavelength range expected to be substantially unabsorbed. As another example, the output signals may convey information related to a difference between intensity in the absorbed wavelength range and the references wavelength range.

In some embodiments, radiation source 60 and sensor assembly 62 may operate to monitor the composition of the measurement flow of the gas drawn through flow path element 28 in the manner described in U.S. Pat. No. 7,748,280, which is hereby incorporated by reference in its entirety.

This description of detector assembly 52 is not intended to be limiting. It will be appreciated that the assembly described and shown may be replaced and/or augmented with other assemblies for detecting relative levels of gaseous constituents. For example, a relative level of oxygen may be monitored with a luminescence quenching assembly that provides electromagnetic radiation into sampling chamber 36, receives electromagnetic radiation emitted by a luminescent material within sampling chamber, and generates output signals providing information related to the received electromagnetic radiation and/or the electromagnetic radiation emitted by detector assembly 52. This type of monitoring is described, for example, in U.S. Pat. Nos. 6,325,978, and 6,632,402, both of which are hereby incorporated by reference into the present application in their entirety.

Pump actuator 54 is configured to releasably engage actuator interface 46 of flow path element 28, and to actuate membrane 44 to create flow through flow path element 28. In some embodiments, actuator interface pump actuator 54 is configured to magnetically couple with actuator interface 46 to secure the engagement therebetween. This is not intended to be limiting.

As is discussed further below with respect to FIGS. 4-6, pump motor 56 is configured to drive pump actuator 54 such that pump actuator 54 actuates membrane 44 to create flow through flow path element 28. The operation of pump motor 56 can be controlled to adjust one or both of pressure and/or flow rate through flow path element 28. For example, one or more operating parameters of the pump motor 56 can be used to infer one or more parameters of the measurement flow of breathable gas through the flow path. Without limitation one or more of current drawn, load (e.g., actuator load, motor load, and/or other loads), position, and/or other operating parameters may be used in this manner. The one or more parameters of the measurement flow of breathable gas may include one or more of pressure, flow rate, volume, and/or other gas parameters. In some embodiments, the one or more parameters of the measurement flow of breathable gas can be directly measured by one or more sensors separate from the pump. Controller 58 is configured to provide processing and/or control functionality within detector device 30. Controller 58 is configured to control operation and/or receive output from both the pump (which includes pump actuator 54 and pump motor 56) and detector assembly 52. By virtue of this integrated control over both subsystems of detector device 30, the footprint, cost, form factor, weight, manufacturability, and/or other features may be enhanced over systems in which the pump and detector assembly 52 are controlled by separate control systems.

Figure 3:
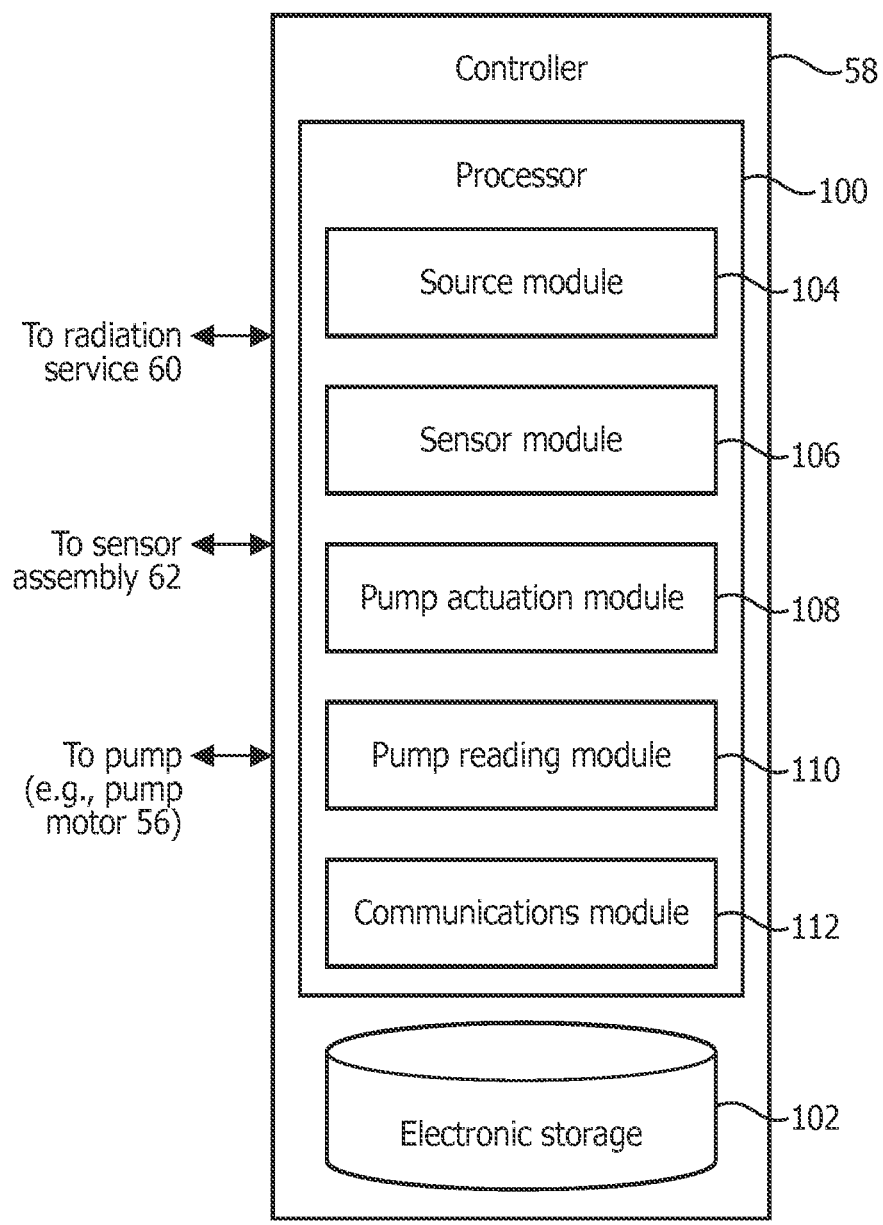
FIG. 3 is a controller configured to control a detector assembly.

FIG. 3 illustrates controller 58, in accordance with some embodiments of this disclosure. As shown, in some embodiments, controller 58 includes one or more of one or more processors 100, electronic storage 102, and/or other components.

Processor 100 is configured to provide processing functionality in controller 58. Processor 100 may include, without limitation, a digital processor, an analog processor, a digital circuit designed to process information, an analog circuit designed to process information, a state machine, and/or other mechanisms for electronically processing information. Processor 100 is configured to execute one or more modules. Processor 100 is configured to execute one or more modules via hardware, software, firmware, some combination of hardware, software and/or firmware, and/or through other mechanisms for configuring processing functionality. The modules may include one or more of a source module 104, a sensor module 106, a pump actuation module 108, a pump reading module 110, a communications module 112, and/or other modules.

Source module 104 is configured to drive radiation source 60. This includes controlling distribution of power to radiation source 60 that will cause radiation source 60 to emit electromagnetic radiation suitable for the detection that will take place within the flow path. For example, source module 104 may control one or more of a level, a current, an amplitude, a frequency of modulation, a voltage, duty cycle, and/or other parameters of power provided to radiation source 60 in order to cause radiation source 60 to emit electromagnetic radiation. The driving of radiation source 60 may be accomplished in a feedback manner based on output signals from sensor assembly 62 and/or a temperature sensor (not shown) disposed at or near radiation source 60 and/or sensor assembly 62.

Sensor module 106 is configured to read the output signals generated by sensor assembly 62. This may include receiving the output signals generated by sensor assembly 62 and processing the output signals prior to transmission of the output signals from controller 58 to some other system (e.g., a monitor unit that presents results to a user). Such processing may include one or more of a signal processing operation (e.g., amplification, digitization, multiplexing, differencing, filtering, and/or other operations), obtaining some measurement or value from the output signals (e.g., to use in feedback operation of radiation source 60, and/or other measurements or values), and/or other processing.

Pump actuation module 108 is configured to drive pump motor 56. This includes controlling distribution of power to pump motor 56. For example, pump actuation module 108 may control one or more of a level, a current, an amplitude, a frequency of modulation, and/or other parameters of power provided to pump motor 56 in order to cause the pump to draw the flow of breathable gas through the flow path. The driving of the pump actuation module may be accomplished in a feedback module to maintain one or more parameters of the flow of breathable gas at a specific level or range of levels. The one or more parameters may include pressure, flow rate, and/or other parameters.

Pump reading module 110 is configured to obtain information related to one or more operating parameters of the pump. Such parameters may include, for example, a rate of operation (e.g., cycles or revolutions per unit time, and/or other rates), an electrical current level driving pump motor 56, and/or other parameters. These parameters may be obtained from a power circuit supplying power to the pump (e.g., under control of pump actuation module 108), from one or more sensors that generate output signals conveying information related to one or more operating parameters of the pump (e.g., an ammeter, a voltmeter, a cycle or revolution sensor, and/or other sensors), and/or from other sources. From the obtained operating parameters, pump reading module 110 may determine one or more of the parameters of the flow of breathable gas through the flow path. For example, pump reading module 110 may determine one or more of a pressure, a flow rate, and/or other parameters of the flow of breathable gas. In some embodiments, a flow and/or pressure sensor (not shown) may be included in the detector device 30 (e.g., as shown in FIGS. 1 and 2), and may provide output signals to pump reading module 110. Pump reading module 110 may use the output signals from this sensor(s) instead and/or in conjunction with the operating parameters of the pump.

Communications module 112 is configured to manage communications between controller 58 and some external monitor device. The external monitor device may include a user interface that enables a user to provide information to and/or receive information from a system that includes detector device 30 (e.g., as shown in FIGS. 1 and 2). The user interface may be used to display, for example, results from the monitoring being performed. The user interface may be used to control operation of detector device 30. For example, detector device 30 may be turned off and/or on through the user interface, and/or controlled in other ways. Communications module 112 may be common for communication of control and/or results directed to and/or generated from output signals of radiation source 60, sensor assembly 62, and the pump. This is a consolidation over embodiments in which the pump and the detector assembly including radiation source 60 and sensor assembly 62 are managed by separate control systems. Typically in such systems communication with the pump and the detector assembly are managed by separate communication modules.

Although processor 100 is shown in FIG. 3 as a single entity, this is for illustrative purposes only. In some embodiments, processor 100 may include a plurality of processing units. However, to maintain the tight integration between the controls for the pump, sensor assembly 60, and radiation source 62, an individual one of the processors included in the processor 100 performs some or all of the functionality of each of source module 104, sensor module 106, pump actuation module 108, and pump reading module 110. The individual processor may further perform some or all of the functionality of communications module 112.

In some embodiments, electronic storage 102 comprises electronic storage media that electronically stores information. The electronic storage media of electronic storage 102 includes system storage that is provided integrally (i.e., substantially non-removable) with controller 58. Electronic storage 102 may include one or more of electrical charge-based storage media (e.g., EEPROM, RAM, etc.), solid-state storage media (e.g., flash drive, etc.), and/or other electronically readable storage media. Electronic storage 102 may store one or more of modules 104, 106, 108, 110, and/or 112, information determined by processor 100, information received from one or more of sensor assembly 62, the pump, and/or other sensors, and/or other information that enables controller 58 to function properly. Electronic storage 102 may be a separate component within controller 58, and/or electronic storage 102 may be provided integrally with one or more other components of controller 58 (e.g., processor 100).

In some embodiments, to maintain the tight integration of control of the pump, radiation source 60, and sensor assembly 62, electronic storage 102 stores (i) at least a portion of one or both of source module 104 and/or sensor module 16, and (ii) at least a portion of one or both of pump actuation module 108 and/or pump reading module 110. In some embodiments, electronic storage 102 includes a single physical block of electronic storage that stores (i) at least a portion of one or both of source module 104 and/or sensor module 16, and (ii) at least a portion of one or both of pump actuation module 108 and/or pump reading module 110. And possibly information read from flow path element 28 including calibration and usage information. As used herein, the single physical block of electronic storage does not refer to a single memory address. Instead, the single physical block of memory refers to an individual memory component (e.g., chip, Flash memory component, and/or other components), or logically bound memory components (e.g., the memory components addressed as a single array of memory).

In some embodiments, controller 58 includes a circuit board (not shown). The circuit board is an integral structure that includes at least some of the components of controller 58, and conductors that interconnect and/or couple the components to allow them to operate properly. Without limitation, the circuit board may include a printed circuit board. To maintain the tight integration of control of the pump, radiation source 60, and sensor assembly 62, the circuit board may be a single board that carries components of controller 58 associated with controlling all of these components. For example, the circuit board may carry all of processor 100 (e.g., all of the individual processors associated with processor 100). As another example, the circuit board may carry an individual processor that performs at least some of all of the functionality of each of modules 104, 106, 108, and 112, and further carries a single physical block of electronic storage that stores (i) at least a portion of one or both of source module 104 and/or sensor module 16, and (ii) at least a portion of one or both of pump actuation module 108 and/or pump reading module 110. Including such electronics on a single circuit board may enhance the footprint, the efficiency, the cost, the manufacturability, and/or other aspects of controller 58. For example, the circuit board carrying the components described in one or both of the foregoing examples may have dimensions that include a length of less than about 4.5 cm, and/or a width of less than about 2.5 cm.

Referring back to FIG. 2, due to the tight integration of control of the pump, radiation source 60, and sensor assembly 62, controller 58 may be housed within a single compartment of housing 40. As used herein, a single compartment does not necessarily refer to a compartment that is wholly sealed off from any other exterior compartment within housing 40. Instead, the single compartment may refer to an individual cavity within housing 40. This cavity may communicate with one or more other compartments within housing 40, but is sufficiently segregated structurally from the other compartments as to form a separate structural compartment. In some embodiments, the volume of this compartment may be less than 12 ml. The dimensions may include one or more of a width of less than about 2.5 cm, a length of less than about 2.5 cm, and/or a depth of less than about 2.0 cm.

By virtue of the integration of control of the pump, radiation source 60, and sensor assembly 62 within controller 58, power to controller 58 for detector device 30 may be received through a single power connection (not shown). The single power connection may couple detector device 30 with a power source that drives radiation source 60, sensor assembly 62, and/or the pump. The power source may be external to detector device 30 and/or internal to detector device 30 (e.g., an internal battery). Distribution of power received through this single power connection may be distributed to radiation source 60, sensor assembly 62, and/or the pump by the controller (e.g., as described above).

Figure 4:
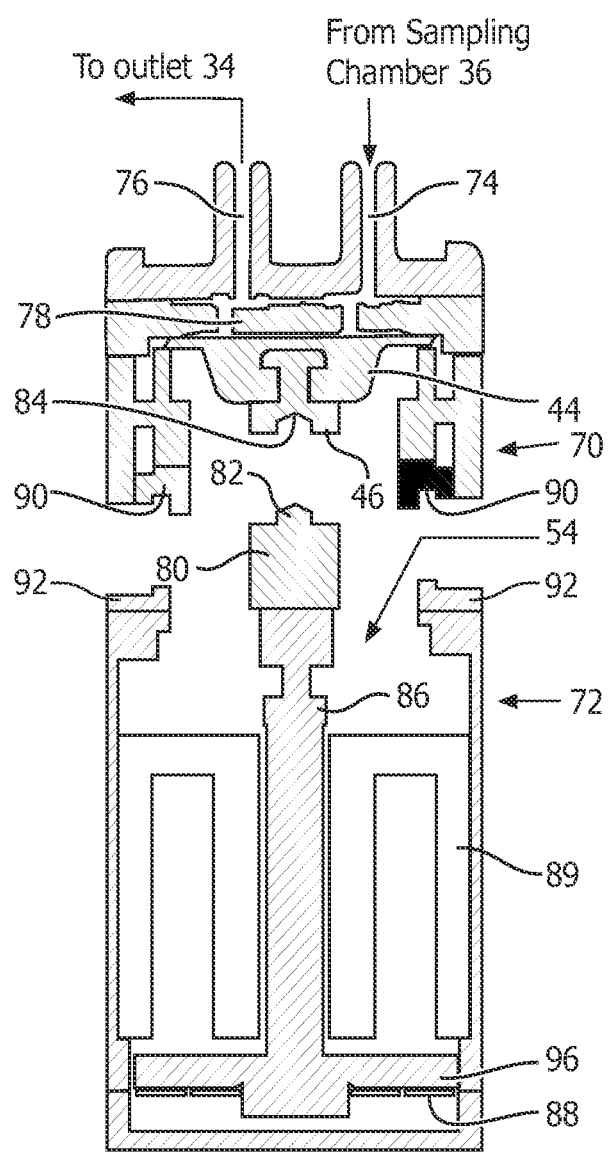
FIG. 4 is a pump configured to draw a flow of breathable gas through a sampling chamber.
Figure 5:
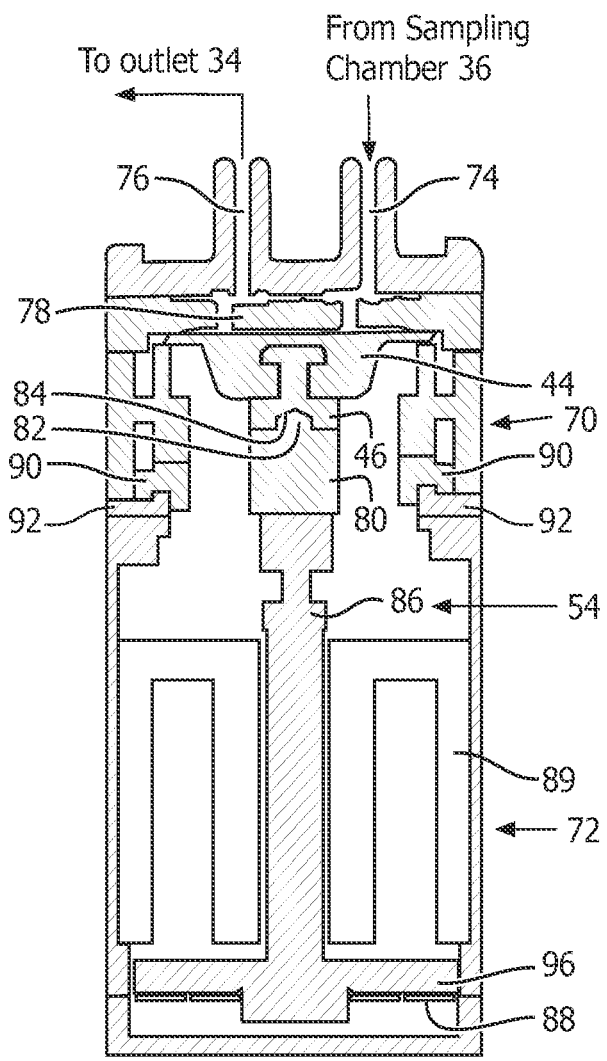
FIG. 5 is a pump configured to draw a flow of breathable gas through a sampling chamber.

FIGS. 4 and 5 illustrate the operation of the pump formed by flow path element 28 and detector device 30, in some embodiments. The pump comprises a pump housing which comprises two parts 70, 72, a first part 70 (formed as a part of pump section 38 in flow path element 28 in FIGS. 1 and 2) in which membrane 44, an inlet 74 and an outlet 76 are arranged, and a second part 72 (formed as a part of detector device 30 in FIGS. 1 and 2) in which pump actuator 54 is arranged. Membrane 44 is mounted to the first part 70 of the pump housing and delimits a pump chamber 78 inside said first part 70. The inlet 74, which has a first non-return valve (not shown) connected thereto, is arranged for feeding the measurement flow of breathable gas into the pump chamber 78, and the outlet 76, which has a second non-return valve (not shown) connected thereto, is arranged for discharging the measurement flow of breathable gas from the pump chamber 78. The pump actuator 54 is configured for moving the membrane 44 back and forth between a first and a second position when the pump is in its assembled form and in use. The membrane 44 is configured to be detachably connected to the pump actuator 54 by means of a magnetic coupling, which comprises actuator interface 46 fixed to the membrane 44 and a corresponding magnetic coupling part 80 fixed to the pump actuator 54. The magnetic coupling can be achieved by having one of the actuator interface 46 and the magnetic coupling part 80 comprising a permanent magnet and the other comprising a ferromagnetic material. The magnetic coupling can of course instead comprise two permanent magnets, one permanent magnet comprised in the actuator interface and one in the magnetic coupling part 80. An electromagnetic coupling is of course also possible. Preferably, the actuator interface 46 comprises a ferromagnetic material and the magnetic coupling part 80 comprises a permanent magnet. The magnetic coupling part 80 also comprises a protrusion 82 configured for insertion into a corresponding recess 84 comprised in the actuator interface 46. Of course a protrusion instead can be comprised in the actuator interface 46 for insertion into a corresponding recess comprised in the magnetic coupling part 80. The pump actuator 54 comprises a shaft 86, which at one end is provided with said magnetic coupling part 80. To move the membrane 44 back and forth the shaft 86 of the pump actuator 54 is driven by a spring, preferably a flat spring 88, longitudinally in one direction and an electromagnet 89 longitudinally in the opposite direction. The spring 88 can of course be replaced by a second electromagnet.

The first part 70 of the pump housing is detachably connected to the second part 72 of the pump housing by means of a coupling, which coupling comprises a first coupling part 90 fixed to the first part 70 of the pump housing and a second coupling part 92 fixed to the second part 72 of the pump housing. The coupling of the pump housing shown in FIGS. 4 and 5 is a magnetic coupling, wherein one of the first 90 and second 92 coupling parts comprises a permanent magnet and the other coupling part comprises a ferromagnetic material. The magnetic coupling can of course instead comprise two permanent magnets, one permanent magnet comprised in the first coupling part 90 and one in the second coupling part 92. Preferably the first coupling part 90 comprises a ferromagnetic material and the second coupling part 92 comprises a permanent magnet. The coupling of the pump housing can also be a snap coupling or any other mechanical or electromechanical coupling suitable for the purpose of connecting the first 70 and the second 72 parts of the pump housing to each other.

The first part 70 of the pump housing is exchangeable (e.g., along with the rest of flow path element 28) and in order to detach it from the second part 72 of the pump housing (and/or detector device 30) said first part 70 is moved in the longitudinal direction of said shaft 86 away from the second part 72 of the pump housing, whereby the actuator interface 46 is detached from the magnetic coupling part 80 and the first coupling part 90 of the pump housing is detached from the second coupling part 92 of the pump housing. If the coupling of the pump housing is a snap coupling or any other coupling, other operations may be needed for detaching the first part 70 of the pump housing from the second part 72 of the pump housing. To attach the first part 70 of the pump housing to the second part 72 of the pump housing the two parts 70, 72 of the pump housing are moved towards each other so as to allow the corresponding coupling parts to come into engagement with each other.

Figure 6:
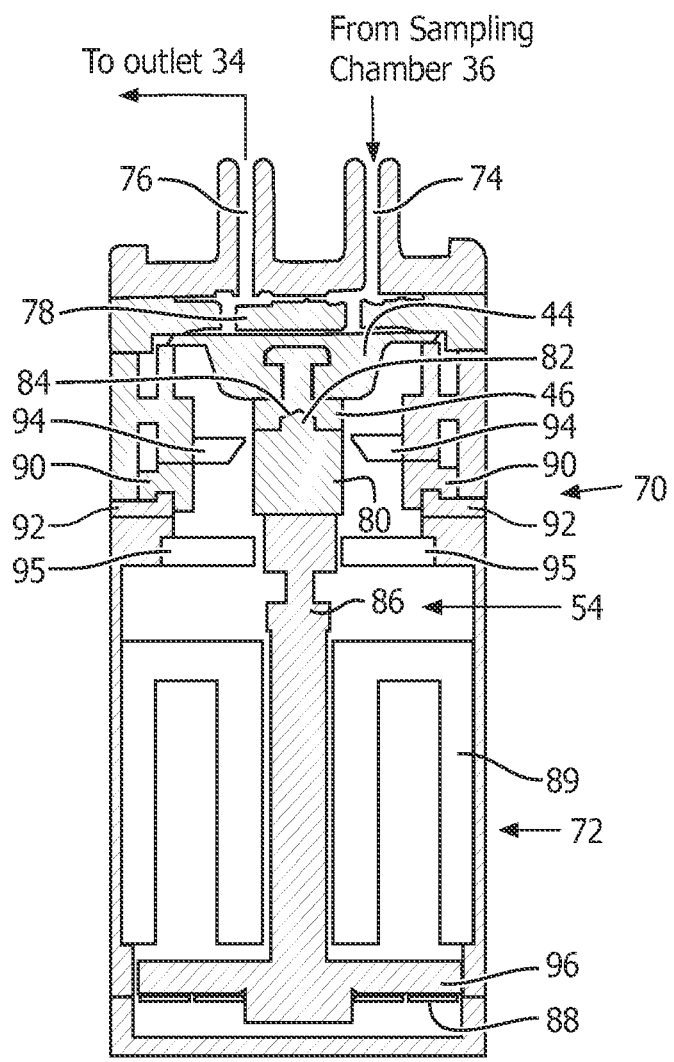
FIG. 6 is a pump configured to draw a flow of breathable gas through a sampling chamber.

In the embodiments illustrated in FIG. 6, the pump comprises guiding means 94 configured for radially guiding the shaft 86 of the pump actuator 54 so as to guide the protrusion 82 of the magnetic coupling part 80 into the recess 84 of the pump actuator 54 when the first part 70 of the pump housing is connected to the second part 72 of the pump housing. The guiding means 94 of the first part 70 of the pump housing has a central opening configured for receiving said shaft 86 and/or the magnetic coupling part 80. The second part 70 of the pump housing comprises guiding means 95 configured for restricting radial movement of the shaft 86 in said second part 72 of the pump housing. The guiding means 95 of the second part 72 of the pump housing is especially important when the first part 70 of the pump housing is detached, due to the risk for damaging the shaft 86 by having it hit the electromagnet 89 if said guiding means 95 is absent. The guiding means 95 of the second part 72 of the pump housing has a central opening configured for receiving said shaft 86.

During pumping using the pumps shown in FIGS. 4-6, in a first phase the flat spring 88 affects the shaft 86, and thereby the membrane 44, with a force pulling the membrane 44 in a direction away from the pump chamber 78, whereby the volume of the pump chamber 78 expands and the first non-return valve is opened so as to allow the measurement flow of breathable gas to flow into the pump chamber 78 through the inlet 74. During this first phase, the membrane 44 is moved under the action of the spring 88 from a first end position to a second end position. In a second phase the electromagnet 89 is activated, whereby the electromagnet 89 attracts a protruding magnetic part 96 of the shaft 86 and the shaft 86 is pulled in a direction towards the pump chamber 78, and the membrane 44 consequently also moves towards the pump chamber 78. The pump chamber 78 is thereby contracted and the measurement flow of breathable gas flows out from the pump chamber 78 through the second non-return valve and the outlet 76. During this second phase, the membrane 44 is moved under the action of the electromagnet 89 and against the action of the spring 88 from the second end position to the first end position. Of course another electromagnet can replace the spring 88 and provide the force for pulling the membrane 44 away from the pump chamber 78. If the spring 88 is replaced by an electromagnet, the other electromagnet 89 can be replaced by another spring, which provides the force for pushing the membrane 44 towards the pump chamber 78. By way of non-limiting example, the pump may operate as described in WIPO publication no. WO2010/128914, which is hereby incorporated by reference in its entirety.

In some embodiments, operation of the pumps shown in FIGS. 4-6 may be precise enough that one or more parameters of the measurement flow of breathable gas can be determined, inferred, and/or adequately estimated without further monitoring. Such parameters may include, for example, pressure, flow rate, and/or other parameters. In some embodiments, one or more detectors may be included with the pumps to directly measurement one or more parameters of the measurement flow of breathable gas. For example, a sensor may be held in second part 72 that contacts membrane 44. The output signals generated by the sensor may indicate one or more of a pressure applied by membrane 44, movement of membrane 44, and/or other parameters. This output signal may facilitate determination of the pressure and/or flow rate of the measurement flow of breathable gas through pump chamber 78. As another non-limiting example, a pressure and/or flow rate detector may be included within first part 70 to directly measure the pressure and/or flow rate of measurement flow of breathable gas. In such embodiments, electrical contacts may be included on first part 70 and/or second part 72 to facilitate communications of the output signals of such detectors to a controller (e.g., controller 58 in FIG. 2).

Figure 7:
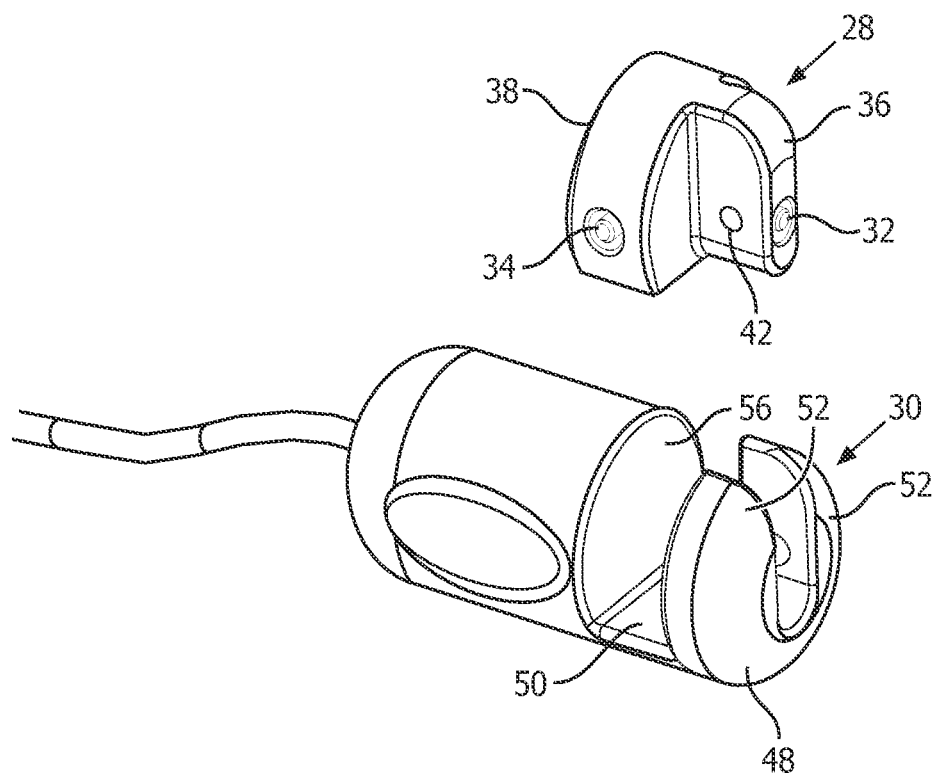
FIG. 7 is a detector assembly and flow path element configured to monitor a composition of a flow of breathable gas.
Figure 8:
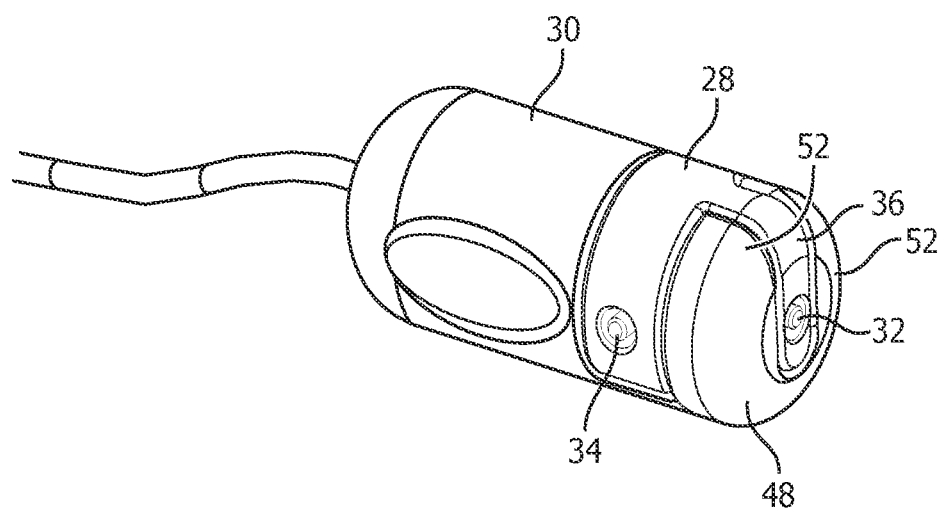
FIG. 8 is a detector assembly and flow path element configured to monitor a composition of a flow of breathable gas.

FIGS. 7 and 8 illustrate flow path element 28 and detector device 30 having different form factors than illustrated in FIGS. 1 and 2. In particular, in the embodiments illustrated in FIGS. 7 and 8, flow path element 28 and detector device 30 have a generally cylindrical shape.

Figure 9:
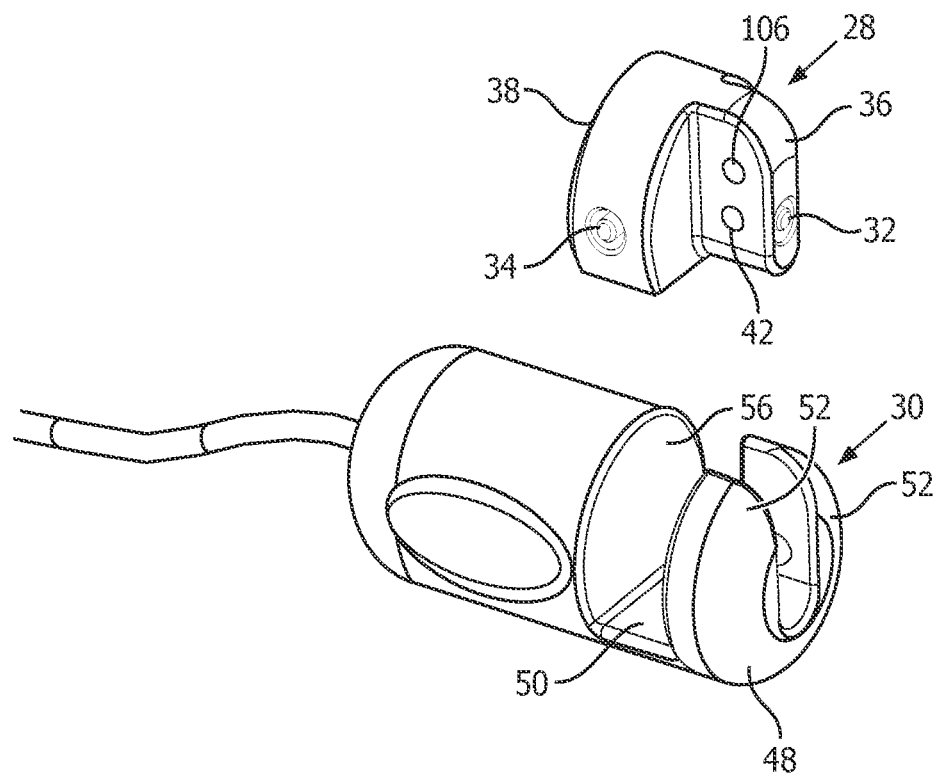
FIG. 9 is a detector assembly and flow path element configured to monitor a composition of a flow of breathable gas.
Figure 10:
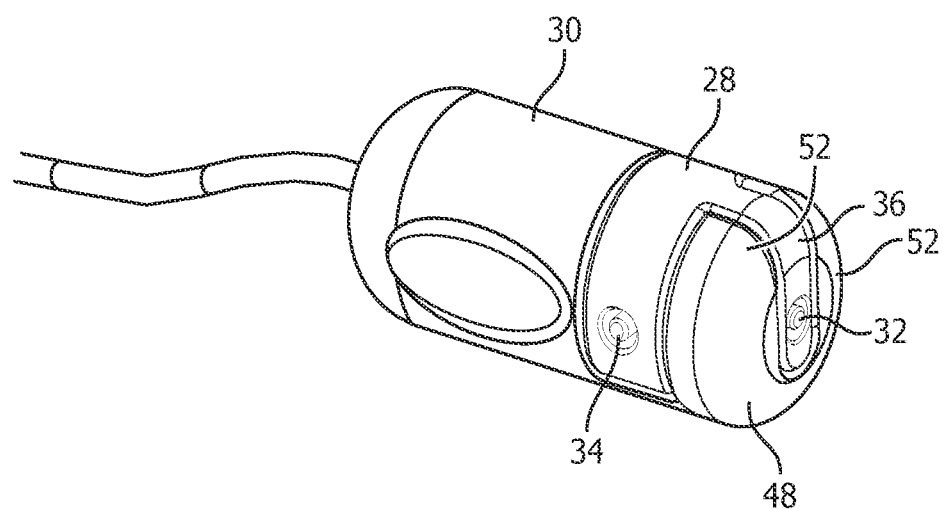
FIG. 10 is a detector assembly and flow path element configured to monitor a composition of a flow of breathable gas.

FIGS. 9 and 10 illustrate one or more embodiments in which detector assembly 52 create a plurality of optical paths through sampling chamber 36. For example, a first optical path may be associated with a sensor assembly designed to determine a relative level of carbon dioxide within sampling chamber 36, and a second optical path may be associated with a sensor assembly designed to determine a relative level of one or more other gaseous constituents using, without limitation, luminescence quenching. To facilitate the second optical path, flow path element 28 includes a window 106 in addition to window 42, to enable electromagnetic radiation to be guided into sampling chamber 36 from two separate radiation sources within detector assembly 52. In such embodiments, control of the further sources and/or sensors associated with determining the relative level of the one or more other gaseous constituents may be tightly integrated with controller 58 (shown in FIGS. 2 and 3 and described above). This may include executing modules associated with the further sources and/or sensors on one or more common processors within controller 58, disposing control electronics for the further sources and/or sensors on a common circuit board of controller 58, storing models associated with the further sources and/or sensors on a common physical block of electronic storage within controller 58, and/or integrating control of the further sources and/or sensors in other ways.

Figure 11:
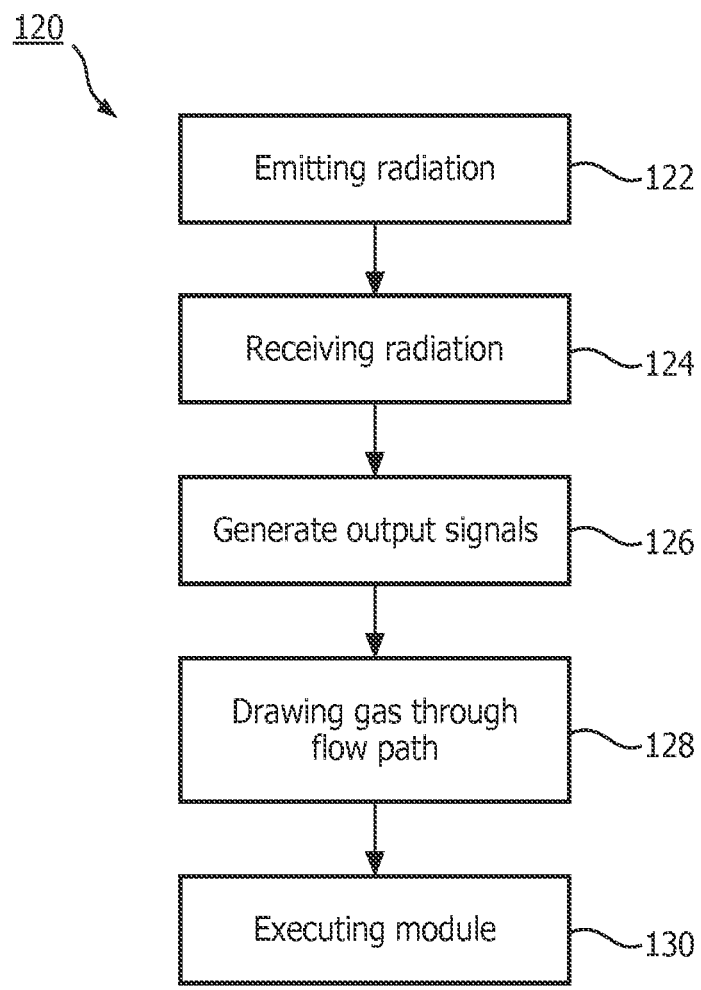
FIG. 11 is a method of monitoring a flow of breathable gas.

FIG. 11 illustrates a method of measuring the composition of a flow of breathable gas received from a respiratory circuit. The operations of method 120 presented below are intended to be illustrative. In some embodiments, method 120 may be accomplished with one or more additional operations not described, and/or without one or more of the operations discussed. Additionally, the order in which the operations of method 120 are illustrated in FIG. 11 and described below is not intended to be limiting.

At an operation 122, electromagnetic radiation is emitted from a radiation source into a flow path for the flow of breathable gas. In some embodiments, the radiation source is the same as or similar to radiation source 60 (shown in FIGS. 1 and 2, and described herein).

At an operation 124, the emitted electromagnetic radiation is received after it has passed through the flow path. In some embodiments, operation 124 is performed by a detector assembly the same as or similar to detector assembly 52 (shown in FIGS. 1 and 2 and described herein).

At an operation 126, output signals are generated by a sensor assembly. The output signals convey information related to one or more parameters of the received electromagnetic radiation. In some embodiments, the sensor assembly is the same as or similar to sensor assembly 62 (shown in FIGS. 1 and 2 and described herein).

At an operation 128, the flow of breathable gas is drawn through the flow path by a pump. In some embodiments, the pump includes a pump actuator and a pump motor that are the same as or similar to pump actuator 54 and pump motor 56 (shown in FIGS. 2 and 3-6 and described herein).

At an operation 130, modules are executed on one or more processors. The modules may be the same as or similar to modules 104, 106, 108, 110, and/or 112 (shown in FIG. 3 and described herein). The processor may be associate with a controller the same as or similar to controller 58 (shown in FIGS. 2 and 3 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A detector device configured to measure composition of a flow of breathable gas received from a respiratory circuit, the detector device comprising:
  a flow path element configured to pass the flow of breathable gas through an interior of the flow path element from an inlet to an outlet, the flow path element including a membrane in a wall thereof, non-return valves disposed upstream and downstream from the membrane, and at least one radiation passing window;
  a housing configured to replaceably receive the flow path element;
  a radiation source mounted within the housing exterior of the replaceably received flow path element and configured to emit electromagnetic radiation through the window into the exterior of the flow path element replaceably received in the housing;
  a sensor assembly within the housing exterior to the flow path element removably received in the housing and configured to receive electromagnetic radiation that has been emitted by the radiation source and has passed through the flow of breathable gas passing through the flow path element, the sensor assembly being further configured to generate output signals conveying information related to one or more parameters of the received electromagnetic radiation;
  a pump motor mounted in the housing; and
  a mechanical pump actuator configured to be driven by the pump motor to engage an exterior of the membrane to pump the flow of breathable gas through the interior of the flow path element; and
  a single control system comprising electronic storage configured to store machine readable instructions and one or more processors mounted within the housing exterior to the removably received flow path element, the one or more processors being configured by the machine-readable instructions to:
    drive the radiation source;
    read the output signals generated by the sensor assembly;
    drive the pump motor;
    obtain information related to one or more operating parameters of the pump motor; and
    communicate with an external user interface.

2. The detector device of claim 1, wherein the one or more processors consist of a single processor.

3. The detector device of claim 1, wherein the one or more processors are carried on a common circuit board.

4. The detector device of claim 3, wherein the common circuit board has a length of less than 4.5 cm, and a width of less than 2.5 cm.

5. The detector device of claim 1, further including a magnetic coupling configured to magnetically couple the pump actuator and the membrane.

6. A method of measuring a composition of a flow of breathable gas received from a respiratory circuit, the method comprising:
  removably mounting a flow path element in a housing, the flow path element including a membrane in a wall thereof, non-return valves disposed upstream and downstream from the membrane, and at least one radiation passing window;
  emitting electromagnetic radiation from a radiation source mounted in the housing and passing through the at least one radiation passing window into the flow path element and the flow of breathable gas;
  with an electromagnetic radiation sensor assembly, receiving the emitted electromagnetic radiation after it has passed through the flow path element and the breathable gas;
  generating output signals with the electromagnetic sensor assembly, the output signals conveying information related to one or more parameters of the received electromagnetic radiation;
  with a pump motor mounted in the housing, driving a pump actuator to engage an exterior of the membrane to pump the flow of breathable gas through the flow path element;
  wherein the radiation source, the electromagnetic radiation sensor assembly, and the pump motor are mounted in said housing; and
  operating a single control system mounted in said housing configured to control the detector device and the pump motor, the single control system comprising electronic storage configured to store machine readable instructions and one or more processors that are contained within a single compartment of the housing, the one or more processors being configured by the machine-readable instructions to:
    drive the radiation source;
    read the output signals generated by the electromagnetic radiation sensor assembly;
    drive the pump motor;
    obtain information related to one or more operating parameters of the pump; and
    communicate with an external user interface.

7. The method of claim 6, wherein the one or more processors consist of a single processor.

8. The method of claim 6, wherein the one or more processors are carried on a common circuit board.

9. The method of claim 8, wherein the common circuit board has a length of less than 4.5 cm, and a width of less than 2.5 cm.

10. The method of claim 6, further including magnetically coupling the flow path element and the housing.

11. A detector device for measuring a composition of a flow of breathable gas received from a respiratory circuit, the detector device comprising:
  a common housing:
  means for defining a flow path for the flow of breathable gas, the flow path defining means being removably mounted to the common housing and including a membrane and non-return valves disposed upstream and downstream from the membrane;
  means mounted in the common housing for emitting electromagnetic radiation into the flow path for the flow of breathable gas;
  means mounted in the common housing for receiving the emitted electromagnetic radiation after it has passed through the flow path and generating output signals that convey information related to one or more parameters of the received electromagnetic radiation;
  a pump motor mounted in the common housing;

a pump actuator configured to be driven by the pump motor to move the membrane to draw the flow of breathable gas through the flow path; and a single control system configured to control the detector device and the pump, the single control system comprising electronic storage and one or more processors housed within an individual compartment within the common housing, the one or more processors being configured by machine-readable instructions stored in the electronic storage to:

drive the radiation source;
read the output signals of the means for generating;
drive the pump motor; and
obtain information related to one or more operating parameters of the pump motor.

12. The detector device of claim 11, wherein the one or more processors consist of a single processor.

13. The detector device of claim 11, wherein the one or more processors are carried on a common circuit board.

14. The detector device of claim 13, wherein the common circuit board has a length of less than 4.5 cm, and a width of less than 2.5 cm.

15. The detector device of claim 11, wherein the flow path defining means is removably mounted in the common housing by means of a magnetic coupling.

16. A detector device configured to measure composition of a flow of breathable gas received from a respiratory circuit, the detector device comprising:

a flow path element configured to pass the flow of breathable gas through an interior of the flow path element from an inlet to an outlet, the flow path element including a membrane in a wall thereof, non-return valves disposed upstream and downstream from the membrane, and at least one window configured to pass radiation;

a housing configured to replaceably receive the flow path element;

a radiation source configured to be replaceably mounted within the housing exterior of the replaceably received flow path element to emit electromagnetic radiation through the window into the exterior of the flow path element;

a sensor assembly removably disposed within the housing exterior to the flow path element and configured to receive electromagnetic radiation emitted by the radiation source and that passed through the at least one window and the flow of breathable gas passing through the flow path element, the sensor assembly being further configured to generate output signals conveying information related to one or more parameters of the received electromagnetic radiation;

a pump motor mounted in the housing; and a mechanical pump actuator configured to be driven by the pump motor to engage an exterior of the membrane to pump the flow of breathable gas through the interior of the flow path element; and a magnetic coupling configured to magnetically couple the pump actuator and the membrane;

guide elements mounted to the housing and configured to guide the mechanical pump actuator to magnetically couple with the membrane;

a control system comprising electronic storage configured to store machine readable instructions and one or more processors the electronic storage and the one or more processors being mounted within the housing exterior to the removably received flow path element, the one or more processors being configured by the machine-readable instructions to:

drive the radiation source;
read the output signals generated by the sensor assembly;
drive the pump motor;
obtain information related to one or more operating parameters of the pump motor; and
communicate with an external user interface.

17. The detector device of claim 1, wherein the flow path element and the housing are configured to connect magnetically.

18. The method of claim 10, further including:
with guide elements mounted to the housing, guiding the pump actuator into contact with the membrane as the flow path element and the housing magnetically couple.

19. The detector device of claim 15, further including:
means for guiding the pump actuator into contact with the membrane as the flow path defining means magnetically couples to the common housing.

20. The detector device of claim 19, wherein the pump actuator magnetically couples with the membrane.

* * * * *